US011986574B2

(12) United States Patent
Taylor

(10) Patent No.: US 11,986,574 B2
(45) Date of Patent: May 21, 2024

(54) SKIN PROTECTANT FILM INCLUDING SKIN HEALTH INGREDIENTS

(71) Applicant: Hollister Incorporated, Libertyville, IL (US)

(72) Inventor: Michael G. Taylor, Mundelein, IL (US)

(73) Assignee: Hollister Incorporated, Libertyville, IL (US)

( * ) Notice: Subject to any disclaimer, the term of this patent is extended or adjusted under 35 U.S.C. 154(b) by 282 days.

(21) Appl. No.: 17/295,800

(22) PCT Filed: Oct. 29, 2019

(86) PCT No.: PCT/US2019/058589
§ 371 (c)(1),
(2) Date: May 20, 2021

(87) PCT Pub. No.: WO2020/112289
PCT Pub. Date: Jun. 4, 2020

(65) Prior Publication Data
US 2022/0001082 A1    Jan. 6, 2022

Related U.S. Application Data

(60) Provisional application No. 62/771,925, filed on Nov. 27, 2018.

(51) Int. Cl.
*A61L 28/00* (2006.01)
(52) U.S. Cl.
CPC ....... *A61L 28/0069* (2013.01); *A61L 28/0011* (2013.01); *A61L 28/0038* (2013.01); *A61L 2300/412* (2013.01); *A61L 2300/45* (2013.01); *A61L 2300/606* (2013.01)

(58) Field of Classification Search
None
See application file for complete search history.

(56) References Cited

U.S. PATENT DOCUMENTS

| | | | |
|---|---|---|---|
| 6,383,502 B1 | 5/2002 | Dunshee et al. | |
| 6,641,821 B1 | 11/2003 | Collin et al. | |
| 2003/0077307 A1* | 4/2003 | Klofta | A61L 15/34 424/401 |
| 2013/0118517 A1* | 5/2013 | Foley | A61Q 1/00 424/60 |
| 2015/0313809 A1* | 11/2015 | Lynch | A61K 8/8129 510/119 |

FOREIGN PATENT DOCUMENTS

EP    0556957 A1    8/1993

OTHER PUBLICATIONS

International Search Report issued by ISA/EPO in connection with PCT/US2019/058589 dated Jan. 3, 2020.
Written Opinion issued by ISA/EPO in connection with PCT/US2019/058589 dated Jan. 3, 2020.
International Preliminary Report on Patentability issued by ISA/EPO in connection with PCT/US2019/058589 dated May 25, 2021.

* cited by examiner

*Primary Examiner* — Dominic Lazaro
(74) *Attorney, Agent, or Firm* — Levenfeld Pearlstein, LLC

(57) ABSTRACT

A no-sting skin protectant film forming composition is formulated with a film forming polymer having both polar and nonpolar characteristics, a no-sting nonpolar solvent system, and at least one skin health ingredient. The no-sting skin protectant film forming composition is configured to form a protective film on a skin surface after the solvent system evaporates.

8 Claims, No Drawings

SKIN PROTECTANT FILM INCLUDING SKIN HEALTH INGREDIENTS

This is a National Stage Application of International Patent Application No. PCT/US2019/058589 filed Oct. 29, 2019, which claims the benefit of and priority to U.S. Provisional Application No. 62/771,925 filed Nov. 27, 2018, the entirety of which are incorporated fully herein by reference.

BACKGROUND

The present disclosure relates to ostomy accessories, and more particularly to skin protectant film forming compositions for peristomal skin.

Many ostomy patients suffer from damaged and irritated skin around a stoma from being in contact with stoma output and using ostomy appliances. For example, peristomal skin may be compromised by adhesive skin stripping when removing ostomy skin barriers. Further, active enzymes in stoma discharge may be corrosive and damage peristomal skin. When damaged or irritated, peristomal skin may weep and become macerated.

Thus, ostomates often use skin protectant film products that adhere to skin and form a barrier to protect skin from stoma output and adhesive skin barriers. Some skin protectant film products include a polymeric film former dissolved in volatile solvents. When applied to skin, the solvents evaporate and a thin protective film is formed on the skin. However, the solvents in these products may produce a stinging sensation when applied to irritated or damaged skin. Further, many of the skin protectant film products include polymers that are generally non-polar and form a film having a relatively low surface energy, which are not easily wet by skin barrier adhesives. As such, adhesion between the skin barrier and the film may be poor and compromise secure attachment of ostomy appliances.

Water based skin protectant film products are also available. However, water is a poor solvent for skin health ingredients, such as ceramide. Further, water based products may not work well with hydrocolloid powder used for forming "crusts" on damaged skin surfaces. When damaged or irritated skin becomes weepy and moist, uniform film formation by such skin protectant film products may become difficult. In such conditions, ostomates often apply hydrocolloid powder before using a skin protectant film product to absorb moisture from broken skin and to form an artificial scab or "crust" to provide a dry surface. However, when a water based product is used with hydrocolloid powder, hydrocolloid powder may absorb water in the skin protectant film product and swell and degrade to compromise adhesion between the skin protectant film and skin.

The present disclosure provides improved skin protectant film forming compositions containing at least one skin health ingredient according to various embodiments.

BRIEF SUMMARY

A composition for forming a film for protecting skin surfaces containing at least one skin health ingredient is provided according to various embodiments. The composition may be a solvent based formulation that does not produce a stinging sensation when applied to an irritated or damaged skin surface and configured to form a film having a sufficiently high surface energy for secure attachment of an ostomy skin barrier while improving skin health. The composition may be water free, such that crusting powder, such as hydrocolloid powder, may be used with the composition.

In one aspect, a no-sting skin protectant film forming composition may contain at least one film forming polymer having both polar and nonpolar characteristics, a no-sting, nonpolar solvent system, and at least one skin health ingredient. The no-sting skin protectant film forming composition may be configured to form a protective film on a skin surface after the solvent system evaporates.

In an embodiment, the at least one film forming polymer may comprise a vinylpyrrolidone-eicosene copolymer. The no-sting, nonpolar solvent system may comprise C7-C8 isoparaffin. The at least one skin health ingredient may comprise ceramide or a blend of ceramide, cholesterol, and stearic acid. The no-sting skin protectant film forming composition may also include alpha-Tocopherol.

In an embodiment, the no-sting skin protectant film forming composition may comprise about 90 weight/weight percent (w/w %) to about 97 w/w % of the no-sting, nonpolar solvent system, about 3 w/w % to about 10 w/w % of the at least one film forming polymer, and about 0.01 w/w % to about 0.05 w/w % of the at least one skin health ingredient. For example, the no-sting skin protectant film forming composition may comprise about 90 w/w % to about 97 w/w % of C7-C8 isoparaffin, about 3 w/w % to 10 w/w % of vinylpyrrolidone-eicosene copolymer, about 0.1 w/w % to about 0.5 w/w % of ceramide 2 based on the vinylpyrrolidone-eicosene copolymer content, cholesterol at a level of about ¼ to about ½ of the number of moles of ceramide 2, and stearic acid at a level of about ¼ to about ½ of the number of moles of ceramide 2. The no-sting skin protectant film forming composition may also include alpha-Tocopherol at a level of about 500 parts per million (ppm) to about 1,500 ppm relative to the vinylpyrrolidone-eicosene copolymer content.

Other aspects, objectives and advantages will become more apparent from the following detailed description.

DETAILED DESCRIPTION

While the present disclosure is susceptible of embodiment in various forms, there will hereinafter be described presently preferred embodiments with the understanding that the present disclosure is to be considered an exemplification and is not intended to limit the disclosure to the specific embodiments illustrated.

A composition for forming a skin protectant film including at least one skin friendly ingredient is provided according to various embodiments. The composition may be formulated as a no-sting solvent based composition including at least one skin friendly ingredient for improving peristomal skin health, e.g. moisturizing, strengthening, smoothening, hydrating, and healing. The composition may be configured to form a flexible, breathable protective film that can provide a good bonding surface for a skin barrier adhesive after rapid evaporation of solvent(s) without causing a stinging sensation even when applied to excoriated skin. The composition may form a breathable barrier film over a weeping peristomal skin surface to protect the skin from stoma output, ostomy appliance adhesive, friction, and other irritants and irritating conditions.

In an embodiment, the composition may generally comprise at least one film forming polymer having both polar and nonpolar characteristics, a no-sting nonpolar solvent system, and at least one skin health ingredient. The composition may be formulated such that a sufficient amount of the film forming polymer may be dissolved in the solvent system to deposit a protective film having a suitable film thickness after the solvent system evaporates relatively rapidly without causing a stinging sensation even on damaged skin.

Suitable solvents for the no-sting nonpolar solvent system may include, but are not limited to, nonpolar hydrocarbon solvents, such as iso-octane. Hexamethyldisiloxane (HMDS) is commonly used in no-sting film forming formulations. However, HMDS is a generally a poor solvent except for silicones, which makes it difficult to form a solution including skin friendly ingredients and film forming polymers dissolved therein. In an embodiment, the no-sting nonpolar solvent system may comprise C7-C8 isoparaffin, such as Isopar™C having a boiling temperature range from 99° C. to 104° C., which is available from ExxonMobil. Isopar™C is well suited for dissolving nonpolar materials, but may have limited solvent capabilities for polar polymers.

Ostomy skin barriers typically do not adhere well to nonpolar surfaces. A protectant film formed from a nonpolar polymer may degrade skin barrier adhesion to render the protectant film not suitable for ostomy applications. After extensive research and development, it was discovered that some copolymers having both polar and nonpolar characteristics and sufficient solubility in a suitable nonpolar hydrocarbon solvent, such as Isopar™C, may work well as a film forming polymer for the composition to provide a skin protectant film that has desirable characteristics including a good bonding surface for skin barrier adhesives. In an embodiment, the at least one film forming polymer may comprise a vinylpyrrolidone-eicosene copolymer including both a polar component, i.e. vinylpyrrolidone, and a nonpolar component, i.e. eicosene, such as Ganex™ polymers available from Ashland.

The at least one skin health ingredient may include materials that protect skin, reduce skin irritation, aid healing, and/or promote skin health. The suitable skin health ingredients may include, but are not limited to, ceramide, cholesterol, stearic acid, vitamin E, vitamin A, vitamin C, aloe vera extract, fatty acids, anti-inflammatory/soothing agents, such as ginkgolide A, hydrolyzed collagen, alpha-amyrin, beta-amyrin, oleanolic acid, and antiperspirants, such as Alcloxa. Oil soluble skin health ingredients, such as oils, butters, and fat soluble vitamins, that are sufficiently soluble in the no-sting nonpolar solvent system may be easily incorporated in the composition. The skin health ingredients may be provided in various forms, for example, fine powder, liquid, or encapsulated, such as encapsulated skin health formulations available from Salvona, of Hamilton, N.J. In an embodiment, the at least one skin health ingredient may comprise a blend of ceramide, cholesterol, and stearic acid, such as a ceramide dominant 3:1:1 blend that includes ceramide, cholesterol, and stearic acid in a 3:1:1 ratio.

In some embodiment, the composition may also include additives for controlling film properties, such as plasticizers for controlling film flexibility.

In an embodiment, the composition for forming a skin protectant film may comprise about 90 weight/weight percent (w/w %) to about 97 w/w %, preferably about 94 w/w % to about 96 w/w % of a no-sting nonpolar solvent system, about 3 w/w % to about 10 w/w %, preferably about 4 w/w % to about 6 w/w % of at least one film forming polymer having both polar and nonpolar characteristics, and about 0.01 w/w % to about 0.05 w/w %, preferably about 0.02 w/w % to about 0.03 w/w % of at least one skin health ingredient.

For example, the composition may be formulated with about 90 w/w % to about 97 w/w %, preferably about 95 w/w % of C7-C8 isoparaffin, about 3 w/w % to about 10 w/w %, preferably about 5 w/w % of vinylpyrrolidone-eicosene copolymer, about 0.1 w/w % to about 0.5 w/w %, preferably about 0.3 w/w % of ceramide 2 based on the vinylpyrrolidone-eicosene copolymer content, and cholesterol and stearic acid, each at a level of about ¼ to about ½, preferably about ⅓ of the number of moles of ceramide 2. The composition may also include alpha-Tocopherol, which is a type of vitamin E, at a level of about 500 parts per million (ppm) to about 1,500 ppm, preferably about 1,000 ppm relative to the vinylpyrrolidone-eicosene copolymer. Alpha-Tocopherol is an antioxidant and may protect the composition for shelf storage.

In an embodiment, the composition may be formulated as a generally clear solution free of solid precipitation. An exemplary composition may comprise about 95 g of C7-C8 isoparaffin, such as Isopar™C, about 5.0 g of vinylpyrrolidone-eicosene copolymer, such as Ganex™ V220F, about 15.5 mg of ceramide 2, about 4.0 mg of cholesterol, about 2.5 mg of stearic acid, and about 5.9 mg of alpha-Tocopherol.

In preparing the exemplary composition, ceramide, cholesterol, and stearic acid were added to Isopar™C, and the suspension was stirred and heated to about 85° C. All of the solids dissolved to yield a clear solution. Upon cooling to room temperature, the solution became turbid as the solids precipitated. Ganex™ V220F was added to the turbid suspension, stirred, and heated to 85° C., whereupon all of the solids dissolved to yield a clear solution. The solution remained clear with little or no evidence of precipitation after seven (7) days at room temperature. Subsequently, alpha-Tocopherol was added at room temperature and stirred, and the solution remained clear with little or no evidence of precipitation or phase separation.

In such embodiments, vinylpyrrolidone-eicosene copolymer, such as Ganex™ V220F, may serve multiple functions, e.g. a film forming polymer, compatibilizer and/or stabilizer for the composition solution.

The film forming composition according to various embodiments of the present disclosure may be provided in a spray bottle, a wipe, or other suitable application vehicles. In use, a user may apply the film forming composition on a peristomal skin surface after cleaning, and allow the solvent system to evaporate. Once the solvent system evaporates and the composition is dried, a flexible, breathable protective film having a sufficiently high surface energy may be formed on the peristomal skin surface for attachment of an ostomy skin barrier. For denuded or weeping peristomal skin, a user may apply crusting powder, such as hydrocolloid powder, followed by the film forming composition to form a flexible, breathable protective film on the crusted peristomal skin.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A no-sting skin protectant film forming composition, comprising:
   about 3 weight/weight percent (w/w %) to about 10 w/w % of at least one film forming polymer having both polar and nonpolar characteristics;
   about 90 w/w % to about 97 w/w % of a solvent system, the solvent system being a no-sting and nonpolar solvent system; and
   about 0.01 w/w % to about 0.05 w/w % of at least one skin health ingredient;
   wherein the no-sting skin protectant film forming composition is provided as a clear solution and configured to form a protective film on a skin surface after the solvent system evaporates.

2. The no-sting skin protectant film forming composition of claim 1, wherein the at least one film forming polymer comprises a vinylpyrrolidone-eicosene copolymer.

3. The no-sting skin protectant film forming composition of claim 1, wherein the solvent system comprises C7-C8 isoparaffin.

4. The no-sting skin protectant film forming composition of claim 1, wherein the at least one skin health ingredient comprises ceramide.

5. The no-sting skin protectant film forming composition of claim 1, wherein the at least one skin health ingredient comprises a blend of ceramide, cholesterol, and stearic acid.

6. The no-sting skin protectant film forming composition of claim 1, further comprising alpha-Tocopherol.

7. A no-sting skin protectant film forming composition of claim 1 comprising about 90 w/w % to about 97 w/w % of C7-C8 isoparaffin, about 3 w/w % to 10 w/w % of vinylpyrrolidone-eicosene copolymer, about 0.1 w/w % to about 0.5 w/w % of ceramide 2 based on the vinylpyrrolidone-eicosene copolymer content, cholesterol at a level of about ¼ to about ½ of the number of moles of ceramide 2, and stearic acid at a level of about ¼ to about 1½ of the number of moles of ceramide 2.

8. The no-sting skin protectant film forming composition of claim 7, further comprising alpha-Tocopherol at a level of about 500 parts per million (ppm) to about 1,500 ppm relative to the vinylpyrrolidone-eicosene copolymer content.

* * * * *